United States Patent [19]

Wade et al.

[11] Patent Number: 5,534,623
[45] Date of Patent: Jul. 9, 1996

[54] PROCESS FOR PREPARING A POLYUNSATURATED DIAZONIUM COMPOUNDS

[75] Inventors: John R. Wade, Leeds; Michael J. Pratt, Ilkley; Jianrong Ren, Leeds, all of United Kingdom

[73] Assignee: Du Pont (UK) Limited, United Kingdom

[21] Appl. No.: 454,486

[22] Filed: May 30, 1995

Related U.S. Application Data

[62] Division of Ser. No. 6,862, Jan. 21, 1993, Pat. No. 5,466,789.

[51] Int. Cl.$^6$ .................................................. C07C 245/20
[52] U.S. Cl. ........................... 534/560; 534/561; 534/564; 534/656
[58] Field of Search .................................. 534/560, 561, 534/565

[56] References Cited

U.S. PATENT DOCUMENTS

| | | | |
|---|---|---|---|
| 2,683,728 | 7/1954 | Mastin et al. | 560/24 |
| 2,958,704 | 11/1960 | Dunbergs et al. | 560/33 |
| 3,211,770 | 10/1965 | Pyne | 560/33 |
| 3,297,745 | 1/1967 | Fehete et al. | 560/26 |
| 3,783,152 | 1/1974 | Larsen | 560/33 |
| 4,233,390 | 11/1980 | Jargiello | 430/156 |
| 4,316,949 | 2/1982 | Petrellis et al. | 430/159 |
| 4,595,648 | 6/1986 | Stanton et al. | 430/561 |
| 4,690,987 | 9/1987 | Sakakibara et al. | 525/502 |
| 4,902,601 | 2/1990 | Potts et al. | 534/561 |
| 4,999,271 | 3/1991 | Etherington et al. | 430/284 |

FOREIGN PATENT DOCUMENTS

| | | | |
|---|---|---|---|
| 84227 | 7/1983 | European Pat. Off. | 560/33 |
| 333645 | 9/1989 | European Pat. Off. | 560/33 |
| 751841 | 7/1956 | United Kingdom | 560/33 |
| 1463818 | 12/1973 | United Kingdom | |
| 2063248 | 8/1980 | United Kingdom | 560/33 |
| 2069997 | 9/1981 | United Kingdom | |
| 2171713 | 9/1986 | United Kingdom | |

OTHER PUBLICATIONS

Roffey, "Photopolymerization of Surface Coatings", John Wiley, New York, pp. 129–130 (1982).

*Primary Examiner*—Fiona T. Powers

[57] ABSTRACT

Polyunsaturated diazonium compounds suitable for use in negative working radiation sensitive compositions are provided. They may be produced by reacting an aromatic diazonium compound of the formula $$(A^-N_2^+)_p\text{—Ar—}(R)_q\text{—}(XH)_r$$

with a polyethylenically unsaturated monoisocyanate compound of the general formula $$\text{OCN—Z—(NHCOY)}_n$$

where p and q are integers ranging from 1 to 5, r is an integer ranging from 1 to 10; Ar represents a substituted or unsubstituted divalent or polyvalent radical derived from an aromatic or heteroaromatic compound; X represents O, S or a secondary or tertiary amino group; R represents a single bond or a substituted or unsubstituted divalent or other polyvalent radical and may be the same or different when q is greater than 1; $A^-$ represents an anion; Z represents the residue of a polyisocyanate $\text{OCN—Z—(NCO)}_n$ where n is 1 or 2; and Y is the residue of a monohydroxy compound of the formula YOH where Y contains at least two ethylenically unsaturated double bonds.

5 Claims, No Drawings

PROCESS FOR PREPARING A POLYUNSATURATED DIAZONIUM COMPOUNDS

This is a division of application Ser. No. 08/006,862, filed Jan. 21, 1993, now U.S. Pat. No. 5,466,789.

This invention relates to polyunsaturated diazonium compounds and is concerned with such compounds suitable for use in negative-working radiation sensitive compositions for the preparation of lithographic printing plates.

Radiation sensitive plates for use in the production of lithographic printing plates comprise a substrate e.g. of suitably treated aluminium, coated with a radiation sensitive composition. In use, the composition is image-wise exposed to actinic radiation which changes the solubility of the areas struck by the radiation. In the case of negative-working compositions the radiation-struck parts become less soluble in developer liquids. Thereafter, the more soluble areas i.e. the non-radiation struck areas are selectively removed by means of developer liquid to leave an image constituted by the less soluble radiation-struck areas.

Photopolymerisable compositions have been widely employed as the radiation-sensitive compositions in negative-working lithographic printing plates. Generally, such printing plates have high durability enabling very long print runs to be completed. Also such printing plates often have high sensitivity allowing very short exposure times to be employed. However, in the case where the photopolymerisable composition depends on a free-radical polymerisation mechanism to cause insolubilisation of radiation-struck areas, a reduction in atmospheric oxygen inhibition of polymerisation must be achieved. Many methods of reducing oxygen inhibition have been discussed in the literature; for instance C. G. Roffey in 'Photopolymerization of Surface Coatings', p129–130 (Wiley, 1982) discloses inter alia barrier layers and amine/benzophenone co-initiators. Applying a second coating, however, is disadvantageous in terms of manufacturing problems and increased costs. Amine co-initiators are often incompatible with acid-group containing binder resins. GB Patents 1463818 and 2171713 describe photopolymerisable compositions containing diazonium resins, which have reduced requirements for barrier layers. U.S. Pat. No. 4,233,390 discloses a photopolymerisable composition in which the diazonium compound is coated as a sub-layer. There are, however, disadvantages associated with such compositions notably: a) incompatibility of the diazonium compound and photopolymerisable compound causing instability and hence poor shelf-life of the composition; b) poor developability in aqueous developers; and c) inferior run length and chemical resistance on printing presses. Commonly used diazonium compounds for example 4-diazo diphenylamine-formaldehyde condensation polymers as the $BF_4^-$ or $PF_6^-$ salts, are sparingly soluble in many common solvents which are conveniently used for coating compositions. Often, hazardous solvents such as glycol ethers need to be used with these resins.

It is an important aspect of photopolymerisable compositions for use in lithographic plate coatings that they contain a compound having at least two, preferably three or more, ethylenically unsaturated groups per molecule in order to achieve efficient polymerisation and crosslinking of areas exposed to radiation in short exposure times. It is also desirable to incorporate groups which confer aqueous solubility on the composition so that the developer liquids need not contain organic solvents. In order to coat the composition satisfactorily and safely, it is necessary for the compounds to have high solubility in a wide range of organic solvents including solvents of low toxicity.

It is an object of the present invention to provide:

i) improved photopolymerisable compounds which have minimal susceptibility to inhibition by oxygen, high photosensitivity, good stability and much higher solubility in a wider range of solvents than is associated with prior art compounds containing diazonium groups;

ii) a method for efficiently synthesising the pure compounds in high yield; and iii) improved radiation sensitive compositions, containing the compounds, which are developable in wholly aqueous developers, have good shelf-life and good printing durability and chemical resistance.

According to one aspect of the present invention, there is provided a polyunsaturated diazonium compound having the general formula 1:

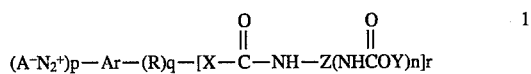

where p and q are integers ranging from 1 to 5 and r is an integer ranging from 1 to 10; and in which Ar represents a substituted or unsubstituted divalent or polyvalent radical derived from an aromatic or heteroaromatic compound; X represents O, S or a secondary or tertiary amino group; R represents a single bond or a substituted or unsubstituted divalent or other polyvalent radical and may be the same or different when q is greater than 1; $A^-$ represents an anion; Z represents the residue of a polyisocyanate OCN—Z—$(NCO)_n$ where n is 1 or 2; and Y is the residue of a monohydroxy compound of the formula YOH where Y contains at least two ethylenically unsaturated double bonds.

Ar may be, for example, phenylene, naphthylene or heteroaromatic radicals such as benzothiazolylene, benzopyrazolylene, or dibenzo-thiazolylene. Ar may also include substituents such as alkyl, aryl, alkoxy, aryloxy, dialkylamino, arylamino, arylamido, arylmercapto, alkylmercapto or styryl groups. Advantages in terms of stability and light sensitivity are conferred by a substituent amino or arylmercapto group in the para position to the diazonium group. The stability may be further increased by the introduction of additional substituents such as alkoxy groups, preferably ortho to the diazonium group.

The radical R may be, for example, a substituted or unsubstituted alkylene, arylene or a combination thereof. The radical R may contain one or more hetoroatoms so as have a structure such as those shown by formulae 2 to 11.

The anion $A^-$ may be, for example p-toluene sulphonate, naphthalene sulphonate, dodecyl benzene sulphonate, dicyclohexylsulphosuccinate, triisopropyl naphthalene sulphonate, diisobutyl naphthalene sulphonate, 2-hydroxy-4-methoxy benzophenone-5-sulphonate, mesitylene sulphonate, octyl phenyl sulphonate, naphthoate, cinnamate, tetrafluroroborate, hexafluorophosphate, or hexafluroroarsenate.

According to another aspect of the present invention, there is provided a preferred process for producing a polyunsaturated diazonium compound as defined in formula 1 which comprises reacting an aromatic diazonium compound of the formula.

with a polyethylenically unsaturated mono isocyanate compound of the formula:

$$\underset{\text{OCN}-Z-(\text{NHCOY})_n}{\overset{\overset{O}{\|}}{}} \quad 26$$

to obtain the ethylenically unsaturated diazonium compound of the present invention wherein p, q, Ar, R, X, r, Z, Y and n have the aforesaid meanings.

The aromatic diazonium compound 12 may be, for example a p-phenylene diamine derivative, an o-phenylene diamine derivative, a compound having a diazo diphenylamine type of structure, or a derivative of a compound containing a primary amine group. Preferred aromatic diazonium compounds are shown by formulae 13 to 25.

The polyethylenically unsaturated mono isocyanate compound of formula 26 is the reaction product of a polyisocyanate of the formula $$\text{OCN}-Z-(\text{NCO})_n \quad 27$$

where n may be 1 or 2, and an ethylenically unsaturated monohydroxy compound of the formula YOH carrying at least two ethylenically unsaturated double bonds.

In formula 27, Z may be, for example, an aromatic, an alicyclic, or a heterocyclic ring. It may also be an alkylene group. Examples of such polyisocyanates are shown by formulae 28–38.

The polyethylenically unsaturated monohydroxy compound of the formula YOH may be of the following detailed general formula:

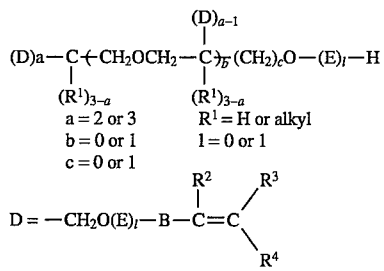

$$R^2 = H \text{ or } CH_3$$
$$R^3 = H \text{ or } CH_3$$
$$R^4 = H \text{ or } CH_3$$
$$R^5 = H \text{ or } CH_3$$
$$R^6 = H \text{ or } CH_3$$

Examples of suitable poly ethylenically unsaturated monohydroxy compounds are glycerol diacrylate, trimethylolpropane diacrylate, pentaerythritol triacrylate, ditrimethylolpropane triacrylate, tetra(hydroxypropyl)pentaerythritol triacrylate, dipentaerythritol pentaacrylate and pentaerythritol triallyl ether.

The ethylenically unsaturated monohydroxy compound of formula 39 is preferably prepared from a saturated polyol by reacting all except one of the hydroxy groups with an ethylenically unsaturated compound including a functional group capable of reacting with a hydroxy group. Such polyols are abundant and suitable examples are glycerol, trimethylolethane, trimethylolpropane, pentaerythritol, dipentaerythritol or polyhydroxyl compounds resulting from the oxyalkylation of polyols with alkylene oxide, in particular ethylene oxide or propylene oxide.

In accordance with a particular embodiment of the invention, the reaction between the polyisocyanate of formula 27 and the polyunsaturated mono hydroxy compound of formula YOH is effected in such a way that the ethylenically unsaturated mono isocyanate compound of formula 26 is produced in a manner such as to avoid the formation of the large amount of by-products which are ordinarily produced when polyisocyanates are reacted with reactive hydrogen-containing compounds. In accordance with this embodiment, the reaction is carried out in a medium in which the reactants are miscible but in which the ethylenically unsaturated mono isocyanate compound is immiscible.

This can be achieved by, for example admixing the hydroxy compound of formula YOH with a solvent with which it is immiscible but with which it becomes miscible when the polyisocyanate is added. Then, as the reaction proceeds and the polyisocyanate concentration decreases, the ethylenically unsaturated mono isocyanate separates out first, thereby preventing further reaction of the remaining isocyanate group. The selective formation of the ethylenically unsaturated mono isocyanate of the invention can be assisted by using, as the polyisocyanate, an isocyanate having isocyanate groups of differing reactivities such as tolylene diisocyanate or isophorone diisocyanate.

Examples of preferred polyunsaturated monoisocyanates are shown by formulae 41 to 44.

According to yet another preferred embodiment, the polyunsaturated diazonium compound is synthesized in accordance with an 'in-situ' process. The polyunsaturated monohydroxy compound of formula 39 is first reacted with a polyisocyanate of the formula 27 in an inert solvent, preferably, with the addition of a suitable catalyst such as dibutyltin dilaurate and a free-radical polymerisation inhibitor such as hydroquinone; then when the designated percentage of the total isocyanate groups have been reacted, without isolating the intermediate, the aromatic diazonium compound of formula 12 is reacted to afford the polyunsaturated diazonium compound of the invention as a viscous liquid.

The following Examples illustrate the invention.

EXAMPLE 1

Synthesis of Compound 41 (a polyacrylate mono isocyanate compound derived from tetra(hydroxypropyl)pentaerythritol triacrylate (THPT) and tolylene-2,4-diisocyanate(TDI))

In a 500 ml three-neck flask equipped with a mechanical stirrer and drying tube, 50 g of tetra(hydroxypropyl) pentaerythritol triacrylate (OH value 113) were stirred in 200 mls of petroleum ether (b.p. 40°–60° C.). Tolylene-2,4-diisocyanate (18.5 g, 0.12 mole, 20% excess) was added dropwise over 10 minutes. On completion of the addition, it was noticeable that THPT was not miscible with the mixture. A minimum amount of diethyl ether was added until a clear solution was obtained. Hydroquinone (0.05 g) and a catalytic amount of dibutyltindilaurate Were added and the reaction mixture was stirred at room temperature for 2 hours and then left standing for 16 hours. A viscous layer, no longer miscible with the solvent mixture, settled out. The top layer of solvents was decanted and the viscous residue washed with petroleum ether three times.

A liquid chromatographic method was used to determine the residual tolylene diisocyanate, and the total isocyanate content of the product was analyzed by titration. A total isocyanate content of 6.3% w/w was found against a theoretical value of 6.4% w/w. Therefore, the purity of the product was 98%.

EXAMPLE 2

Synthesis of Compound 42 (a polyacrylate mono isocyanate compound derived from THPT and isophorone diisocyanate (IPDI))

50 g of THPT (OH value 113) were reacted with isophorone diisocyanate (22.42 g, 0.1 mole) in a mixture of petroleum ether (b.p. 40°–60° C.) and diethyl ether according to the method of Example 1. A total isocyanate value of 5.6% w/w was found against a theoretical value of 5.8% w.w. Therefore, the purity of the product was 96.5%.

EXAMPLE 3

Synthesis of Compound 43 (a polyallyl ether mono isocyanate compound derived from pentaerythritol triallyl ether and TDI)

50 g of pentaerythritol triallyl ether (OH value 220) were reacted with 34 g of TDI (0.196 mole) in petroleum ether (b.p. 40°–60° C.) according to the method of Example 1. A total isocyanate content of 9.0% w/w was found against a theoretical value of 9.3% w.w. Therefore, the purity of the product was 96.7%.

EXAMPLE 4

Synthesis of Compound 44 (a polyacrylate mono isocyanate derived from dipentaerythritol pentaacrylate (DPEPA) and TDI)

50 g of dipentaerythritol pentaacrylate (OH value 110) was reacted with TDI (20 g, 0.12 mole, 20% excess) in a mixture of petroleum ether (b.p. 40°–60° C.) and diethyl ether according to the method of Example 1. A total isocyanate value of 5.8% w/w was found against a theoretical value of 6.1% w.w. Therefore, the purity of the product was 95%.

EXAMPLE 5

Synthesis of compound 45 (a polyacrylate diazonium compound derived from compound 41 and diazo -4(N-ethyl-N-hydroxy butyl)phenylene diamine hexafluorophosphate Diazo-4(N-ethyl-N-hydroxybutyl)phenylene diamine hexafluorophosphate (7.3 g, 0.02 mole) was dissolved in 50 mls of dry methyl ethyl ketone with the addition of hydroquinone (0.01 g) and a catalytic amount of dibutyltin dilaurate. 13.5 g, 0.02 mole, of compound 41 were dissolved in 20 mls of dry methyl ethyl ketone and added dropwise to the solution over a period of 30 minutes. The mixture was then stirred at 25° C. until monitoring showed the residual isocyanate was all reacted. Methanol (5 mls) was added and the mixture further stirred for 2 hours. The solvent was then removed in vacuo to produce a viscous liquid.

UV spectroscopy and IR were employed to confirm the structure of the final product.

EXAMPLE 6

Synthesis of Compound 46 (a polyacrylate diazonium compound derived from compound 44 and diazo-3-(2-hydroxyethoxy diphenylamine hexafluorophosphate)

Diazo-3-(2-hydroxyethoxy)diphenylamine hexafluorophosphate (8.0 g 0.02 mole) was reacted with compound 44 (14.5 g, 0.02 mole) according to the method in Example 5. Ultraviolet and infrared spectroscopy confirmed the structure of the product.

EXAMPLE 7

A solution in methyl ethyl ketone comprising:

2.55 parts of Compound 45;

0.85 parts of poly(vinyl butyral)hydrogen phthalate ester having an acid value of 85;

0.125 parts of 2-(p-methoxyphenyl)-4,6 -bistrichloromethyl-s-triazine; and 0.2 parts of Victoria Pure Blue FGA was whirler coated onto a sheet of electrograined and anodised aluminium to give a coating weight of 1.0 gm$^{-2}$. The resultant radiation sensitive plate was exposed through a continuous tone Stouffer stepwedge to ultraviolet light (200 mJcm$^{-2}$ in a Berkey-Ascor frame) and then developed with an aqueous solution containing sodium propanoate, sodium benzoate and a surfactant. A solid step 5, tail 7 was reproduced on the stepwedge. A second exposure was carried out in a similar way but without contact vacuum being applied. A solid step 4, tail 7 was reproduced. When placed on a printing press the plate achieved 150,000 satisfactory impressions.

EXAMPLE 8

(Comparative)

The method of Example 7 was repeated except that tetra(hydroxy propyl)pentaerythritol triacrylate (THPT) was used instead of Compound 45. After a similar vacuum exposure and development process, a solid step 4, tail 7 was reproduced. However, the same exposure without contact vacuum gave no image.

EXAMPLE 9

A solution in methyl ethyl ketone comprising:

1.3 parts of Compound 45;

1.0 parts of poly(vinylbutyral)hydrogenphthalate ester of Example 7;

0.1 parts of 2-(p-methoxyphenyl),4,6-bistrichloromethyl-s-triazine; and 0.07 parts of Victoria Pure Blue FGA was whirler coated onto a sheet of electrograined and anodised aluminum to give a coated weight of 1.2 gm$^{-2}$. The resultant radiation sensitive plate was exposed through a continuous tone Stouffer stepwedge to UV light (200 mJcm$^{-2}$ in a Berkey-Ascor frame), and then developed with an aqueous solution containing sodium propanoate, sodium benzoate and a surfactant. A solid step 5, tail 8 was reproduced. A similar exposure without contact vacuum gave the same stepwedge reading. When placed on a printing press, the plate produced 200,000 satisfactory impressions. Samples of plate were subjected to accelerated ageing tests in a humidity cabinet at 30° C. and 95% relative humidity.

After five weeks storage, the plate still developed to leave a clean unstained background.

EXAMPLE 10

(Comparative)

A solution in 2-methoxy ethanol comprising:

1.0 parts of dipentaerythritol pentaacrylate;

1.0 parts of the poly(vinylbutyral)hydrogen phthalate of Example 7;

0.3 parts of 4-diazodiphenylamine-formaldehyde hexafluorophosphate condensation polymer;

0.1 parts of 2(p-methoxyphenyl)4,6-bistrichloromethyl-s-triazine; and 0.07 parts of Victoria Pure Blue FGA was whirler coated onto electrograined and anodised aluminium to give a coating weight of 1.2 gm$^{-2}$. Exposure with vacuum (200 mJcm$^{-2}$) and developer containing 3% benzyl alcohol was required to fully develop background areas. A similar exposure without vacuum gave a solid 4, tail 9 stepwedge reading. When placed on a printing press the plate produced 180,000 satisfactory impressions. However, when subjected to the accelerated ageing conditions in Example 9, the plates would not develop after one week storage.

EXAMPLES 11–13

The formulations shown in Table 1 were coated from 2-methoxyethanol onto electrograined and anodised aluminium to give coating weights of 1.1–1.3 gm$^{-2}$. The resultant radiation-sensitive plates where then exposed to UV light in a frame through a Stouffer stepwedge and developed with an aqueous solution containing sodium propanoate, sodium benzoate and a surfactant. The results are shown in Table 2.

TABLE 1

| | Example | | |
|---|---|---|---|
| Component | 11 | 12 | 13 |
| Compound 46 | 1.0 | — | — |
| Poly(vinylbutyral)hydrogen phthalate* | 1.5 | 1.5 | 1.4 |
| DPEPA | — | 1.0 | 0.9 |
| 4-DDP | — | — | 0.3 |
| MPT | 0.08 | 0.08 | 0.08 |
| Victoria Pure Blue FGA | 0.08 | 0.08 | 0.08 |

*as described in Example 7
DPEPA = dipentaerythritol pentaacrylate
4-DDP = 4-diazodiphenylamine-formaldehyde condensate PF$_6^-$ salt
MPT = 2-p-methoxyphenyl)-4,6-bis(trichloromethyl)-s-triazine

TABLE 2

| Example | Vacuum | Stepwedge (200 mJcm$^{-2}$) | Background | Number of impressions |
|---|---|---|---|---|
| 11 | Yes | 5, 10 | Clean | 200,000 |
| | No | 4, 10 | Clean | — |
| 12 | Yes | 4, 8 | Clean | 140,000 |
| | No | No image | Clean | — |

TABLE 2-continued

| Example | Vacuum | Stepwedge (200 mJcm$^{-2}$) | Background | Number of impressions |
|---|---|---|---|---|
| 13 | Yes | 5, 11 | Heavy stain | 180,000 |
| | No | 4, 9 | Heavy stain | — |

EXAMPLE 14

Synthesis of Compound 47 (a polyacrylate diazonium compound derived from Compound 41 and 4,4'-bisdiazo-2,2',5,5'-tetrahydroxydiphenylmethane)

4,4-Bisdiazo-2,2',5,5'-tetrahydroxydiphenylmethane, prepared according to French Patent 794,776, (11,52 g,0.02 mole) was reacted with Compound 41 (29,2 g,0.08 mole) according to the method in Example 5. Ultraviolet and infrared spectroscopy and NMR confirmed the structure of the product.

EXAMPLE 15

Synthesis of Compound 48 (a polyacrylate diazonium compound derived from Compound 41 and 2-amino-5-methoxy-6-diazobenzothiazole)

2-Amino-5-methoxy-6-diazobenzothiazole (5,12 g.0.02 mole) prepared according to German Patent 1,106,171 was reacted with Compound 41 (7.3 g,0.02 mole) according to the method in Example 5. Ultraviolet and infrared spectroscopy and NMR confirmed the structure of the product.

EXAMPLE 16

A solution in methylethylketone comprising:

2.6 parts of Compound 45

0.9 parts of an acrylic binder (methyl methacrylate/ethyl acrylate/acrylic acid copolymer, acid value 100).

0.15 parts of 2-(4-methoxy naphthyl)-4,6-bistrichloromethyl-s-triazine; and 0.2 parts of Victoria Pure Blue FGA was whirler coated onto a sheet of electrograined and anodised aluminium to give a coating weight of 0.9 gm$^{-2}$. The resultant radiation sensitive plate was exposed through a continuous tone Stouffer stepwedge to UV light (200 mJcm$^{-2}$ in a Berkey-Ascor frame) and then developed with an aqueous solution containing sodium propionate, sodium benzoate and a surfactant. A solid step 5, tail 8 was reproduced. The printing plate thus formed had excellent ink receptivity and when placed on a printing press it completed 140,000 satisfactory impressions.

EXAMPLE 17

Example 16 was repeated except that the binder was replaced by the same amount of a copolymer of styrene, methacrylic acid, ethyl acrylate and methylmethacrylate, acid value 70. The plate was exposed and developed as described in Example 16 and gave similar results when placed on a printing press.

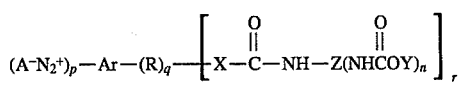 (1)
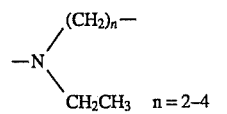 (2)
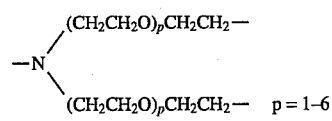 (3)
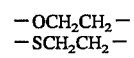 (4) (5)
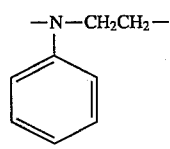 (6)
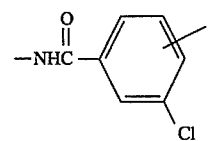 (7)
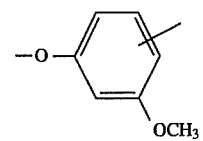 (8)
 (9)
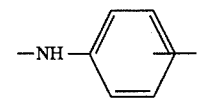 (10)
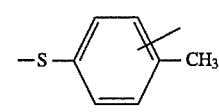 (11)
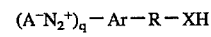 (12)
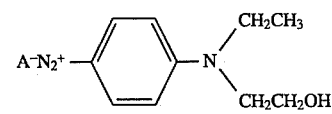 (13)
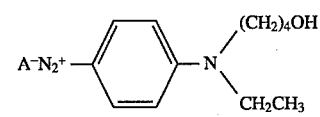 (14)
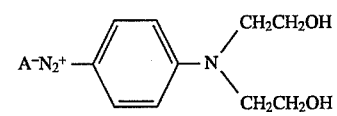 (15)
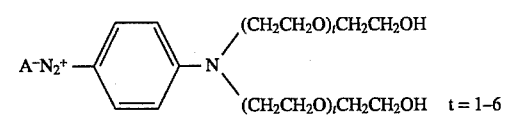 (16)

-continued
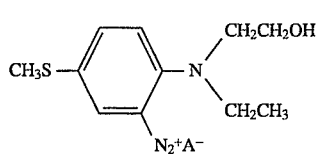 (17)
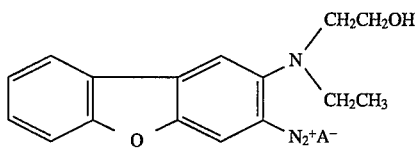 (18)
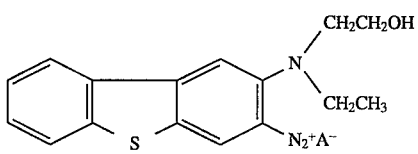 (19)
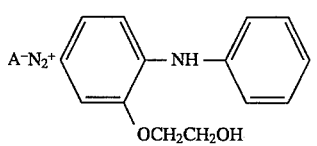 (20)
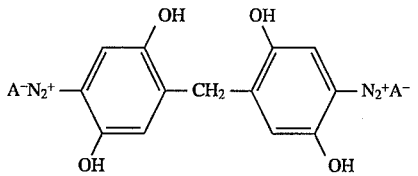 (21)
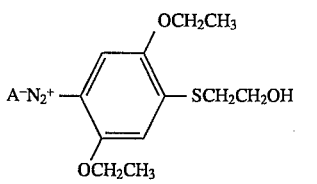 (22)
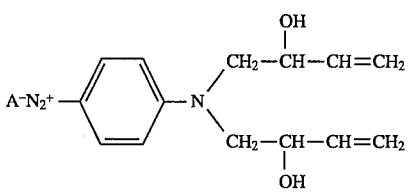 (23)
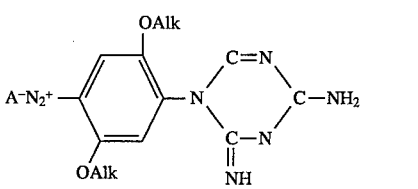 (24)
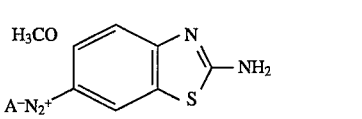 (25)
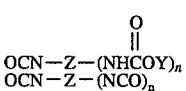 (26)
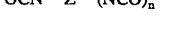 (27)

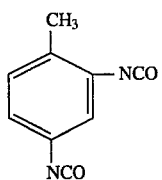 (28)
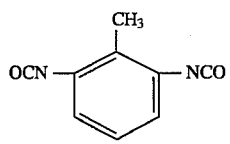 (29)
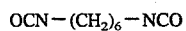 (30)
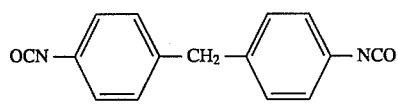 (31)
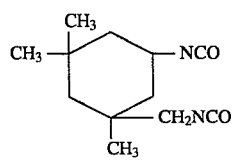 (32)
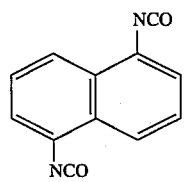 (33)
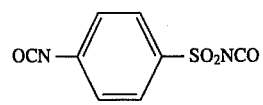 (34)
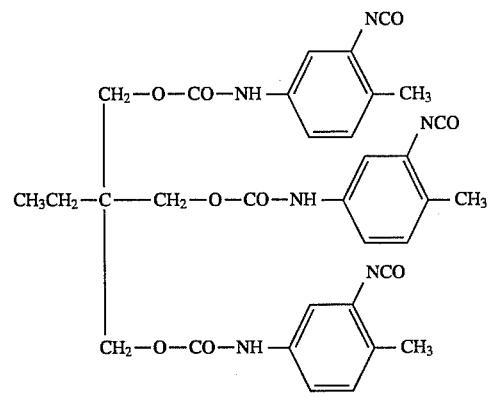 (35)
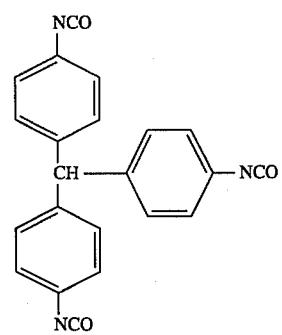 (36)

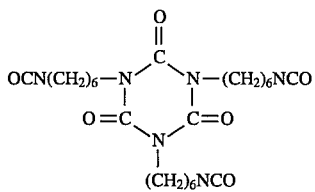 (37)
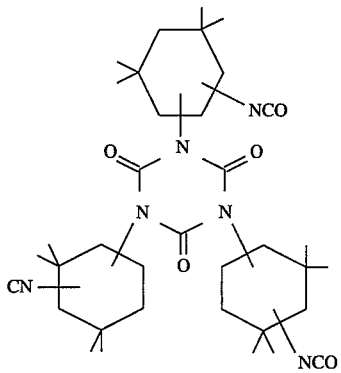 (38)
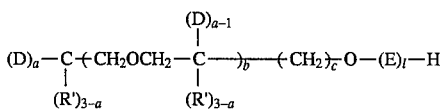 (39)
a = 2 or 3    R' = H or alkyl
b = 0 or 1    l = 0 or 1
c = 0 or 1
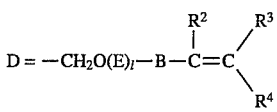 (40)
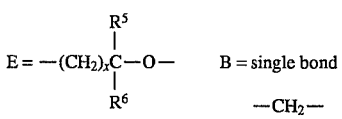
x = 1–3
$R^2$ = H or $CH_3$
$R^3$ = H or $CH_3$
$R^4$ = H or $CH_3$
$R^5$ = H or $CH_3$
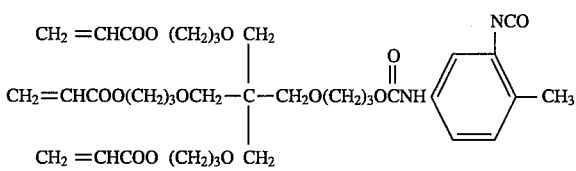 (41)
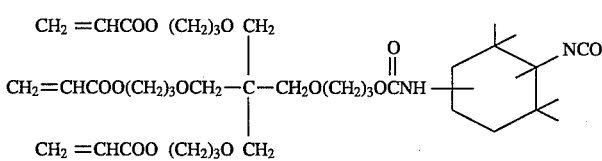 (42)
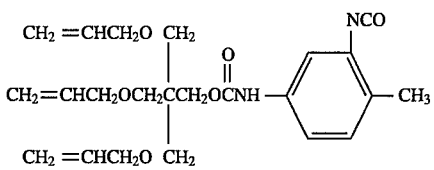 (43)

-continued
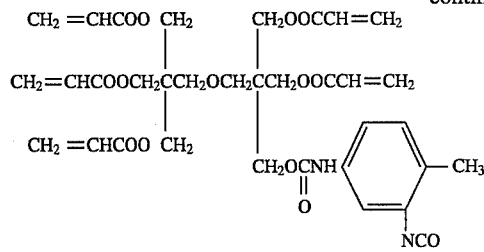
(44)
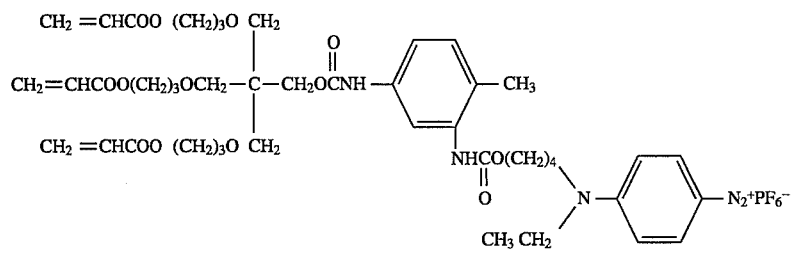
(45)
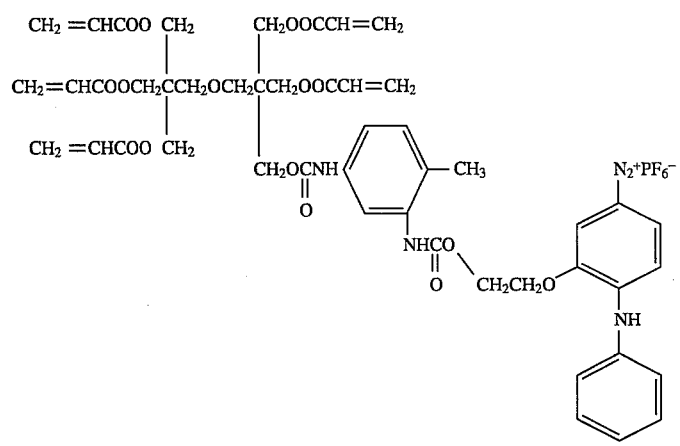
(46)
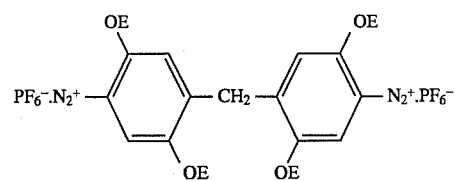
(47)
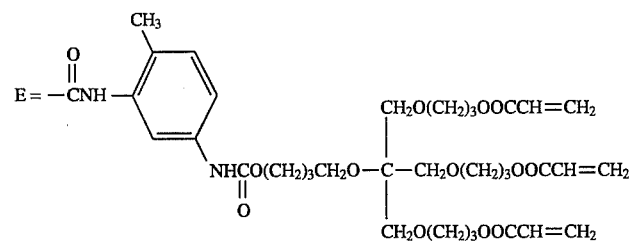
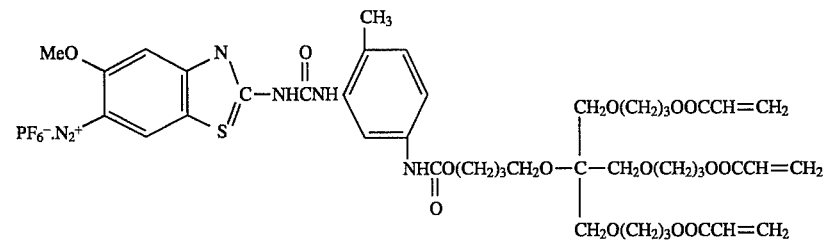
(48)
We claim:
1. A process for producing a polyunsaturated diazonium compound comprising the steps of:
(a) reacting a polyisocyanate of the formula:
OCN—Z—(NCO)$_n$ wherein Z is selected from the group consisting of an aromatic, an alicyclic, or heterocyclic ring or an alkylene group, and n is 1 or 2, and an ethylenically unsaturated monohydroxy compound YOH wherein Y contains at least two ethylenically unsaturated double bonds to form a polyethylenically unsaturated mono-isocyanate compound of the formula:

$$OCN-Z-(NHCOY)_n$$

wherein Z, Y, and n have the aforesaid meanings, said reaction being conducted in a medium wherein said polyisocyanate and said ethylenically unsaturated monohydroxy compound are miscible but the resulting polyethylenically unsaturated mono-isocyanate compound is immiscible; and (b) reacting said polyethylenically unsaturated mono-isocyanate compound of step (a) with an aromatic diazonium compound of the formula:

$$(A^-N_2^+)_p-Ar-(R)_q-(XH)_r$$

to produce the polyunsaturated diazonium compound; wherein p and q are integers ranging from 1 to 5; r is an integer ranging from 1 to 10; Ar is a substituted or unsubstituted divalent or polyvalent radical derived from an aromatic or heteroaromatic compound; X is oxygen, sulfur, or a secondary or tertiary amino group; R represents a single bond or a substituted or unsubstituted divalent or other polyvalent radical and may be the same or different when q is greater than 1; and $A^-$ is an anion.

2. A process of claim 1 wherein the aromatic diazonium compound 12 is a p-phenylene diamine derivative, an o-phenylene diamine derivative, a diazo diphenylamine derivative, or a primary aromatic or heterocyclic amine derivative.

3. A process according of claim 1 wherein the polyisocyanate is tolylene diisocyanate or isophorone diisocyanate.

4. A process of claim 1 wherein the ethylenically unsaturated monohydroxy compound has the formula:

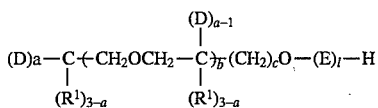

a=2 or 3  $R^1$=H or alkyl
b=0 or 1  l=0 or 1
c=0 or 1

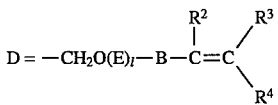

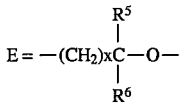

B=single bond or

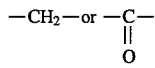

x=1-3
$R^2$=H or $CH_3$
$R^3$=H or $CH_3$
$R^4$=H or $CH_3$
$R^5$=H or $CH_3$
$R^6$=H or $CH_3$.

5. A process of claim 1 wherein the ethylenically unsaturated monohydroxy compound is glycerol diacrylate, trimethylolpropane diacrylate, pentaerythritol triacrylate, ditrimethylolpropane triacrylate, tetra(hydroxypropyl)pentaerylthritol triacrylate, dipentaerythritol pentaacrylate or pentaerythritol triallyl ether.

* * * * *